(12) United States Patent
Brown et al.

(10) Patent No.: US 6,783,768 B1
(45) Date of Patent: Aug. 31, 2004

(54) METHOD AND APPARATUS FOR THE COATING OF SUBSTRATES FOR PHARMACEUTICAL USE

(75) Inventors: Steven R. Brown, Kent (GB); Linda A. Reeves, Kent (GB); John N. Staniforth, Bath (GB)

(73) Assignee: Phoqus Pharmaceuticals Limited, Kent (GB)

( * ) Notice: Subject to any disclaimer, the term of this patent is extended or adjusted under 35 U.S.C. 154(b) by 0 days.

(21) Appl. No.: 09/310,740

(22) Filed: May 13, 1999

Related U.S. Application Data

(63) Continuation of application No. PCT/GB97/03113, filed on Nov. 13, 1997.

(30) Foreign Application Priority Data

Nov. 13, 1996 (GB) ............................................. 9623634

(51) Int. Cl.[7] .......................... A61K 9/70; A61K 47/00; B05B 5/00; B65B 23/00; B05C 19/00; B05D 1/06; B05D 1/36; B05D 3/00

(52) U.S. Cl. ........................... 424/443; 118/13; 118/15; 118/20; 118/35; 118/37; 118/106; 118/123; 118/621; 424/439; 427/154; 427/289; 427/355; 427/372.2; 427/375; 427/458; 427/470; 427/472; 427/474; 427/475; 427/482; 427/487

(58) Field of Search ................................. 427/458, 470, 427/472, 475, 482, 487, 154, 289, 372.2, 375, 355, 457, 459, 460, 471, 474, 477, 483, 532, 577, 559, 356, 402; 424/443, 439, 464, 468, 472; 118/13, 15, 20, 35, 37, 621, 106, 123

(56) References Cited

U.S. PATENT DOCUMENTS

| | | | |
|---|---|---|---|
| 2,698,814 A | | 1/1955 | Ransburg ..................... 427/481 |
| 3,764,538 A | * | 10/1973 | Shelffo ........................ 430/109 |
| 3,900,000 A | | 8/1975 | Gallen ......................... 118/630 |
| 4,029,757 A | * | 6/1977 | Mlodozeniec et al. ........ 424/27 |
| 4,176,175 A | | 11/1979 | Maekawa et al. ........... 424/480 |
| 4,201,834 A | | 5/1980 | Hannon et al. ............. 428/407 |
| 4,349,531 A | | 9/1982 | Mlodozeniec et al. ...... 424/452 |
| 4,454,125 A | | 6/1984 | Demopoulos ................ 514/52 |
| 4,482,387 A | | 11/1984 | Wood et al. ................. 106/270 |
| 4,547,571 A | | 10/1985 | Mukohyama et al. ......... 536/40 |
| 4,548,825 A | | 10/1985 | Voss et al. .................. 426/383 |
| 4,704,295 A | | 11/1987 | Porter et al. ............... 427/2.21 |
| 4,786,505 A | | 11/1988 | Lovgren et al. ............ 424/468 |
| 4,800,079 A | | 1/1989 | Boyer |
| 4,810,501 A | | 3/1989 | Ghebre-Sellassie et al. 424/469 |
| 4,828,840 A | | 5/1989 | Sakamoto et al. |
| 4,925,670 A | * | 5/1990 | Schmidt ...................... 424/443 |
| 4,994,273 A | | 2/1991 | Zentner et al. ............. 424/422 |
| 5,011,694 A | | 4/1991 | Nuernberg et al. ......... 424/464 |
| 5,076,706 A | | 12/1991 | Shibuya et al. ............. 366/349 |
| 5,206,030 A | | 4/1993 | Wheatley et al. ........... 424/490 |
| 5,320,796 A | | 6/1994 | Harashima et al. ......... 224/349 |
| 5,411,730 A | | 5/1995 | Kirpotin et al. .......... 424/9.322 |
| 5,436,026 A | | 7/1995 | Berta et al. ................. 427/214 |
| 5,474,786 A | | 12/1995 | Kotwal et al. |
| 5,540,995 A | | 7/1996 | Kitano et al. ............... 428/407 |
| 5,699,649 A | * | 12/1997 | Abrams et al. ............... 53/428 |
| 5,792,513 A | | 8/1998 | Koslow et al. ............. 427/195 |
| 6,117,479 A | | 9/2000 | Hogan et al. ............... 427/214 |

FOREIGN PATENT DOCUMENTS

| | | |
|---|---|---|
| DE | 2 247 701 | 4/1974 |
| DE | 3106984 A1 | 2/1982 |
| DE | 30 49 179 A | 7/1982 |
| EP | 0 020 181 A | 12/1980 |
| EP | 063 014 A | 10/1982 |
| EP | 0 011 268 | 12/1982 |
| EP | 0 164 959 A2 | 5/1985 |
| EP | 0 220 670 A2 | 5/1987 |
| EP | 0 259 749 A | 3/1988 |
| EP | 0 259 749 A1 | 3/1988 |
| EP | 0 277 741 A1 | 8/1988 |
| EP | 0 307 642 | 3/1989 |
| EP | 0 452 862 A2 | 10/1991 |
| EP | 0 459 048 | 12/1991 |
| EP | 0 536 791 A | 4/1993 |
| EP | 551 700 A | 7/1993 |
| EP | 0 567 201 | 10/1993 |
| EP | 0 661 091 A | 7/1995 |
| EP | 0 678 561 | 10/1995 |
| FR | D 24.084 | 11/1966 |
| FR | 0 107 557 | 5/1984 |
| GB | 1 075 404 | 7/1967 |
| GB | 561 100 | 2/1980 |
| GB | 1 561 100 A | 2/1980 |
| GB | 2 056 885 A | 3/1981 |
| GB | 2 065 691 A | 7/1981 |
| GB | 2 179 254 A | 3/1987 |
| GB | 2 203 336 A | 10/1988 |
| GB | 2 241 889 A | 9/1991 |
| LU | 52 460 A | 6/1968 |

(List continued on next page.)

OTHER PUBLICATIONS

Chem. Abs. 120, 20m 253268 (Grosvenor) (1994).

Diss. Abstr. Int. 53, 7, 1991, Bath, 3492 (1995).

Kirk Othmer, Encyclopedia of Chemical Technology, vol. 19, 1982, 3rd Ed., p1–2.

*Primary Examiner*—Thurman K. Page
*Assistant Examiner*—Frank Choi
(74) *Attorney, Agent, or Firm*—Nixon & Vanderhye

(57) ABSTRACT

Method of coating a substrate which is a belt, sheet, film, or tape, comprising applying an active coating material to the substrate to form an active coating layer, the active coating material comprising biologically active material. The active coating material is applied electrostatically as a powder and, after the active coating material is applied, the active coating material is fused to form an active film layer. The active coating material is removable from the substrate as a wafer comprising the active film layer.

118 Claims, 3 Drawing Sheets

FOREIGN PATENT DOCUMENTS

| | | |
|---|---|---|
| WO | 91/16041 | 10/1991 |
| WO | WO 91/16041 * | 10/1991 |
| WO | 91 16041 A | 10/1991 |
| WO | 92/11002 | 7/1992 |
| WO | 92/14451 | 9/1992 |
| WO | 94/05263 | 3/1994 |
| WO | 94/11446 A | 5/1994 |
| WO | 96/02236 | 2/1996 |
| WO | 96/11707 | 4/1996 |
| WO | 96/35413 | 11/1996 |
| WO | 96 35413 A | 11/1996 |
| WO | 96/39256 | 12/1996 |
| WO | 96/39257 | 12/1996 |
| WO | 97/04827 | 2/1997 |
| WO | 97/37775 | 10/1997 |
| WO | 97/37803 | 10/1997 |
| WO | 97/38480 | 10/1997 |
| WO | 97/47346 | 12/1997 |
| WO | 97/47347 | 12/1997 |
| WO | 99/06593 | 2/1999 |
| WO | 99/06814 | 2/1999 |
| WO | 99/13817 | 3/1999 |

* cited by examiner

METHOD AND APPARATUS FOR THE COATING OF SUBSTRATES FOR PHARMACEUTICAL USE

This application is a continuation of PCT application No. PCT/GB97/03113, filed Nov. 13, 1997.

The present invention relates to methods of coating by substrates, to apparatus for coating substrates and to coated substrates for pharmaceutical use. In particular, but not exclusively, the invention relates to the coating of pharmaceutical substrates to produce solid dosage forms.

BACKGROUND OF THE INVENTION

It is to be understood that the term "solid dosage form" is to be interpreted in a broad sense as covering a wide variety of pharmaceutical products. Thus the term covers pharmaceutical products to be taken orally, for example, pharmaceutical tablets of conventional shape as well as capsules and spherules and tablets of unconventional shape. The term also covers pharmaceutical products not taken orally, for example, a pessary, a bougie, a suppository or a patch for application to the skin. Also, where reference is made to "pharmaceutical substrate" it is to be understood that the term covers the substrates of the solid dosage forms indicated above. The term "solid dosage form" does not, however, include pharmaceutical products such as small pellets and granules, for example small pellets which are filled into capsule shells for administration and granules which are compressed to form tablets; such pellets or granules are not themselves each solid dosage forms but rather, when combined together in a capsule or tablet, define in combination a solid dosage form.

It will be understood that the term "active material" and "active component" used throughout the specification includes material which is biologically active and will comprise one or a mixture of pharmaceutical materials. The pharmaceutical materials include those materials which are administered for the prevention and/or treatment of disease.

Active materials are conventionally administered in the form of tablets.

In a conventional method of producing a pharmaceutical tablet, a mixture containing the biologically active ingredient together with diluents such as lactose and other ingredients is mixed and portions of the mixture are formed into discrete tablets by, for example, pressing samples of the mixture.

A problem with the method of producing tablets described above is that, due to inhomogeneity of the mixture from which the tablet cores are made, the amount of active ingredient in the resulting tablet cores varies from one tablet to the next. While that is a problem for all types of tablet core produced in that way, it is a particularly serious problem when the amount of active ingredient in each core is low, for example for active compounds of high activity. In that case a small absolute variation in the percentage amount of active ingredient in the cores corresponds to a significant variation in the dose contained in each tablet which is clearly most undesirable.

In one known method, a coating solution containing active material is applied to the surfaces of small beads using conventional spray coating techniques, for example by spraying the coating solution towards the beads as they are tumbled in a revolving drum. The coated beads are filled into capsule shells for administration. Such a method is not appropriate for use where accuracy in the amount of the active material applied to the cores is required because there is little control over the amount of coating material applied to each core using that method.

Active components are often administered in tablet form. As indicated above, conventional tablets include a small amount of active component and a large amount of diluent such as lactose so that the tablet is a convenient size. The tablet is a convenient way for the active component to be administered because each tablet contains a predetermined metered dose of the active material.

However, some patients find the taking of tablets difficult, for example because of their size or because of the presence of the other ingredients in the tablet composition. Thus an alternative dosage form would be desirable.

GB 1 561 100 describes the coating of a web with material containing an active ingredient. The coated web is processed to internalize the active coating by, for example, lamination and winding to provide a dosage form.

It is an object of the invention to overcome or mitigate one or more of the above mentioned disadvantages.

In accordance with the invention, there is provided a method of coating a substrate, the method including the steps of applying an active coating material to the substrate to form an active coating layer, the active coating material comprising biologically active material, wherein the active coating layer is removable from the substrate.

In accordance with the invention, the active material is applied as a coating to a substrate from which it can be removed.

In one alternative embodiment of the invention, the coating material is applied directly onto a surface of the coating apparatus, the coating formed in the process being removed from the apparatus as a wafer containing the active material.

In a second alternative embodiment of the invention, the coating material is applied onto a substrate, the coating being removed from the substrate as a wafer, for example by a patient prior to the administration of the material. The substrate may be, for example, a sheet comprising plastics material, for example low adhesion plastics material.

The surface of the substrate may be precoated with one or more coating layers.

Preferably, the active coating material is applied electrostatically. There are various advantages in applying coating materials electrostatically, for example, reduction in waste of coating material, improved coating efficiency and improved coating weight uniformity.

In one alternative of the invention, the active coating material is applied in the form of a dry powder.

Advantageously, at least 90% by weight of the particles of the active coating material have a particle size less than 200 $\mu$m.

Advantageously, at least 90% by weight of the particles of the active coating material have a particle size between from 1 to 200 $\mu$m. Preferably, at least 90% by weight of the particles of the active coating material have a particle size between from 1 $\mu$m to 100 $\mu$m. The term "particle size" refers to the equivalent particle diameter of the particles and may be measured using, for example, laser light diffraction. The particle size of the powder is an important factor in powder coating techniques. If the particles of the powder are very small, the powder will often be too cohesive for successful powder application using many powder coating techniques. However, large particles can be disadvantageous because they are often more difficult to coat onto a surface and, if the coating material is to be fused after application to the surface, longer fusing times may be required, leading to increased risk of damage to the substrate and to the active component.

Where reference is made to by weight of particles, for example the by weight of particles having a particular size, the particles will also preferably have that by volume of particles of that size.

Alternatively, the coating material may be applied in the form of a liquid.

Advantageously, the active coating material further includes one or more excipients. The formulation will usually consist of the active component and a mixture of excipients that will aid in the coating of the material. The formulation may also include other components, for example, colorants and/or flavourings and/or agents to control the rate of release of the active component.

Advantageously, the substrate is conveyed through a region adjacent to a source of the active coating material. That allows the method to be continuous.

In one advantageous embodiment of the invention, the method comprises supporting the substrate adjacent to the source of the active coating material with a surface of the substrate maintained at such a different electric potential from that of the active coating material that the application of the electric potential causes the active coating material to move from the source of the active coating material towards the substrate, a surface of the substrate becoming coated with the active coating material.

Preferably, the substrate is supported from above and the powder moves from the source upwards towards a lower surface of the substrate.

Preferably, the substrate is charged when the substrate is adjacent the source of the active coating material. Alternatively, or in addition, the source of active coating material may be charged.

The method may further include the step that after the active coating layer is applied the active coating material is treated to form an active film coating secured to the surface of the substrate. Where the coating material is in the form of a powder material, the treatment advantageously comprises a heating step, preferably by infra red radiation, but other forms of electromagnetic radiation may be used. Usually, the change in the coating upon heating will simply be a physical change from a powder to a liquid and then, on cooling, to a solid coating, but there are other possibilities: for example, the powder coating may comprise a polymer which is cured during the treatment step, for example by irradiation with energy in the gamma, ultra violet or radio frequency bands, to form a cross-linked polymer coating.

The method may further include the step of applying a cover coating layer onto the active coating layer to form a cover coating layer such that the active coating layer is substantially completely covered by the cover coating layer.

The active coating material applied to the surface of the substrate might not be treated to form an active film coating. A cover coating layer applied subsequently over the active coating material could be used to seal the active coating on the surface of the substrate.

Where the coating material is in the form of a liquid, the treatment advantageously comprises drying the coating material with a heater although other methods could be used.

The coating material containing the active component is susceptible to damage at high temperatures and it is therefore particularly important that the temperature of treatment is dot high. Advantageously, the temperature of treatment is less than 250° C., preferably less than 200° C. and more preferably less than 150° C. Where the higher treatment temperatures are used, the duration of the treatment is advantageously short to reduce the possibility of damage of the coating material.

Preferably, the cover coating material is applied electrostatically. The cover coating material may be in the form of a powder. The cover coating material may also include active material. The active material in the cover coating may be the same as or different from the active material in the active coating layer.

Advantageously, at least 90% by weight of the particles of the cover coating material have a particle size between from 1 to 200$\mu$m.

Preferably, the substrate is conveyed through a region adjacent to a source of the cover coating material.

In one advantageous embodiment of the invention, the method comprises supporting the substrate adjacent to the source of the cover coating material with a surface of the substrate maintained at such a different electric potential from that of the cover coating material that the application of the electric potential causes the cover coating material to move from the source of the cover coating material towards the substrate, a surface of the substrate becoming coated with the cover coating material.

Advantageously, the substrate is supported from above and the powder moves from the source upwards towards a lower surface of the substrate.

Preferably, the substrate is charged when the substrate is adjacent to the source of the cover coating material. Alternatively, or in addition, the source of cover coating material may be charged.

Advantageously, the method further includes the step that after the cover coating layer is applied the cover coating material is treated to form a film coating secured to the surface of the substrate. The treatment of the cover coating layer may be similar to that of the active coating layer described above.

In an embodiment of the invention the active coating layer covers only part of a surface of the substrate. In that embodiment, the cover coating layer may cover only part of a surface of the substrate, or alternatively may cover the whole surface of the substrate.

The cover coating layer may be applied by depositing powder which thereafter forts a layer over the active coating layer or by applying a preformed sheet or film over the active coating layer.

The method may further include the step of applying a further coating material to a surface of the substrate to form a further coating layer. The further coating material may include biologically active material, the further coating layer forming a further active coating layer and the method may further include the step of applying a further cover coating material onto the further active coating layer to form a further cover coating layer such that the further active coating layer is substantially completely covered by the further cover coating layer.

Thus substrates having two or more different active components may be produced. The cover coating material covering the first active coating may be different from that covering the second active coating so that the rate of release of the first active component may be different from that of the second active component. Alternatively, the two active components maybe the same and the cover coatings may be the same or different materials. One or more of the cover coating materials may contain active material.

Advantageously, the method is continuous. In practice, there are considerable advantages in being able to operate the coating process continuously rather than as a batch process.

Advantageously, the active coating material is applied to a part of a surface of the substrate, the active coating layer forming a first active coated region on the surface of the substrate. Where, for example, a plurality of coating layers are to be applied to each substrate, each coating layer forms a coated region on a part of the substrate.

Thus the method may include the further step of applying a second active coating layer onto a surface of the substrate, the second active coating layer forming a second active coated region on a surface of the substrate.

Preferably, the method further includes the step of applying a cover coating material onto the active coating layer to form a cover coating layer such that the active coating layer is substantially completely covered by the cover coating layer and such that the cover coating layer is removable from the substrate. Depending on the nature of the cover coating material, the cover coating layer may be removable together with the active coating layer or may be removable separately. The cover coating layer provides a cosmetic coating and may also protect the active coating material. The cover coating material may also include active material which may be the same as or different from the active material of the active coating layer. The cover coating may comprise a preformed film or sheet of material which is applied over the active coating.

Where more than one active coating layer is applied to the substrate, the method preferably further includes the step of applying a second cover coating layer onto the second active coating layer to form a second cover coating layer such that the second active coating layer is substantially completely covered by the second cover coating layer, the second cover coating layer being substantially separate from the first cover coating layer.

The invention also provides a method of coating a plurality of coating regions onto the surface of a substrate, the method comprising the steps of:
(a) applying active coating material to a surface of the substrate to form a plurality of active coating regions on the surface comprising active coating layers, the active coating material including biologically active material
(b) applying cover coating material to a surface of the substrate to form a plurality of cover coating regions, the cover coating regions forming layers of cover coating material, each active coating region being substantially completely covered by a cover coating region, such that each region of active coating and cover coating is removable from the surface of the substrate.

Advantageously, the method further includes the step of removing that active coating layer from the substrate to form a wafer comprising active material. Each wafer may comprise a single dose of active component. Alternatively, the wafer may be subsequently cut to form wafer portions, each wafer portion including substantially a dose of active material.

Where reference is made to the quantity of active coating material being substantially equal to a dose of the active material, it will be understood that the quantity may be a fraction of the single standard dose, for example ½ or ⅓ of a single standard dose of the active material. It will be understood that the quantity of active material will depend on the active component used and the number of solid dosage forms to be taken by the patient for each dose. Where more than one layer of the active coating material is to be applied to each substrate, the quantity of active component in each layer will be chosen accordingly.

The invention also provides apparatus for coating a substrate according to a method as described above.

The first aspect of the invention also provides an apparatus for coating a substrate, the apparatus comprising:
(a) a source of active coating material,
(b) support means for supporting a substrate adjacent to the source of the active coating material such that the active coating material forms an active coating layer on a surface of the substrate.

Advantageously, the apparatus further comprises:
(c) a source of a cover coating material,
(d) means for conveying the substrate having the active coating layer to a position adjacent to the source of cover coating material such that the cover coating material forms a cover coating layer which substantially completely covers the active coating layer.

The apparatus advantageously includes means for applying the active coating material and/or the cover coating material electrostatically. As indicated above, the coating material may be applied in the form of a dry powder or in the form of a liquid.

Advantageously, the substrate comprises a conveyor belt.

Advantageously the apparatus further includes means for applying a charge to the source of active coating material. The charge can be adjusted to change the amount of coating material applied to the substrate.

Advantageously, the apparatus further includes charging means for applying a charge to the substrate. The charge may be applied using a corona charge wire adjacent to the substrate or by arranging a charged plate adjacent to the substrate. The charged substrate attracts coating material from the source onto the surface of the substrate. Thus it is possible to obtain a very thin uniform layer of coating material on the substrate surface.

Preferably, the source is arranged below the conveyor.

Also provided by the present invention is an apparatus for coating a substrate, the apparatus comprising:
(a) a source of coating material
(b) means for moving the substrate relative to the source of coating material,
(c) means for applying an active coating material onto a surface of the substrate to form a plurality of active coating regions,
(d) means for applying a cover coating material onto the surface of the substrate to form a plurality of cover coating regions such that each active coating region is substantially completely covered by a cover coating region, the coating materials being applied such that the active coating material is removable from the surface of the substrate.

The invention also provides a coated substrate comprising an active coating layer on a surface of the substrate, the active coating layer including biologically active material and in which the active coating layer is removable from the surface of the coated substrate.

In one embodiment of the invention, each active coating layer comprises a quantity of biologically active material which is substantially equal to one dose or, for example, one half dose of the biologically active material. It will be understood that the quantity of active component will depend on the active material used and the required dose.

Alternatively the active coating layer may subsequently be cut into small portions.

Preferably, the substrate further includes a cover coating layer on a surface of the substrate, the cover coating layer substantially completely covering the active coating layer in which the cover coating layer is removable from the surface of the substrate. As indicated above, the cover coating layer may be removable separately from the active coating layer.

The substrate may include a plurality of active coating layers forming active coating regions on a surface of the substrate.

Preferably, each active coating region includes a cover coating region comprising a layer of cover coating material in which each active coating region is substantially completely covered by a cover coating region.

In one alternative embodiment of the present invention, for example where the active coating material is applied as a liquid, the active coating material is applied as a metered dose to a surface of the substrate. to form an active coating layer on the surface.

Very accurate application of the coating material on each surface can be obtained.

This is to be contrasted with the known methods where coating material is sprayed towards the cores. In that case the amount of coating material applied to each substrate depends on many factors all of which would require close control if accurate application is to be achieved. It will be understood that whilst reference is made to applying a metered dose, that should not be taken to imply that there is necessarily any measurement of the amount of material applied. A metered volume of liquid may be applied to each substrate.

Advantageously, a predetermined number of droplets of active coating material are applied to the surface of the substrate. Thus where the droplets are of the same size, the number of droplets applied to the substrate surface determines the amount of active material applied. By altering the number of droplets applied, the apparatus can easily be adapted to apply the required quantity of active material.

Advantageously the coating method is such that the coefficient of variation of the quantity applied to each substrate or region of the substrate is not more than 15%.

As indicated above, where the coating material includes active material, the accuracy and reproducibility of the application of the material to the substrates is of particular importance. For known spraying techniques such as those described above, the coefficient of variation can be 50% or more. Whilst that is acceptable where the coating is a cosmetic coating, it is not acceptable where the coating contains active material. Preferably the coefficient of variation is not more than 10%, and most preferably 3% or less.

Advantageously, the active coating material is applied in the form of individual liquid droplets which are propelled from the supply directly towards a surface of the substrate.

As indicated above, where the material is applied as a plurality of individual droplets, it is more simple to alter the dose of active material applied to the substrate by changing the number of droplets applied. Thus advantageously, the number of droplets applied is controllable.

An ink jet head may be used in the coating of the substrates with active coating material. A conventional ink jet head, for example those used for ink jet printers, can be used to apply an easily controllable amount of material from the head onto a substrate.

In one embodiment of the invention, the area of the surface of the substrate covered by the active coating layer is less than 40% of the total surface area of the substrate. The area covered by the active coating layer may be less than 25% of the total surface area of the substrate. The active coating may form a plurality of small coated regions on the surface of the substrate.

Thus the active coating layer may cover only apart of the exposed surface of the substrate.

Where the quantity of active material to be administered using each solid dose is small, as indicated above, it is advantageous for the proportion of active component in the active coating material to be large.

By covering a smaller proportion of the surface of the substrate, a smaller amount of coating material may be used. Thus the proportion of active component in the coating material may be increased.

The active coating material may be applied to a plurality of individual regions of the surface of the substrate.

The invention also provides a method of coating a substrate, the method comprising applying an active coating material to a surface of the substrate to form an active coating layer, the active coating material comprising biologically active material, applying a cover coating over the exposed surfaces of the active coating layer and dividing the substrate to form substrate portions, each substrate portion including substantially one dose of the active material.

The invention also provides a pharmaceutical solid dosage form comprising a substrate and an active coating layer covering less than 25% of the surface area of the substrate the active coating layer comprising biologically active material.

The coating layer may be shaped, for example to form a pattern, a picture, symbols, letters or numerals.

The invention also provides a wafer for administration to a patient, the wafer comprising biologically active material and having a thickness of less than 2 mm. Preferably the thickness is less than 1 mm.

The invention further provides an intermediate product for use in producing a plurality of solid dosage forms, the intermediate product comprising a substrate and an active coating layer deposited on the substrate, the amount of active coating material deposited on a given area of the substrate being controlled such that the product can subsequently be divided into portions with each portion containing a predetermined amount of active coating material, each predetermined amount being one dose of the active material.

In accordance with a further aspect of the invention, there is provided a method of coating a substrate, the method comprising applying an active coating material to a surface of the substrate to form an active coating layer, the active coating material comprising biologically active material, applying a cover coating layer over the exposed surfaces of the active coating layer and dividing the layered product to form layered portions, each layered portion including substantially one dose of the active material.

In accordance with the further aspect of the invention, the active coating material can be such that it is not removed from the substrate. For example, the active material might be applied to an edible film which can be administered orally.

It will be understood that the method of coating may further include features of the method of the first aspect of the invention described herein. Furthermore, it will be appreciated that the apparatus and coating materials described in respect of the first aspect of the invention could be used in the method in accordance with the further aspect of the invention, with minor modifications where necessary.

BRIEF DESCRIPTION OF THE DRAWINGS

Embodiments of the invention will now be described by way of example having reference to the drawings of which.

DETAILED DESCRIPTION OF PREFERRED EMBODIMENTS

Figure 1:
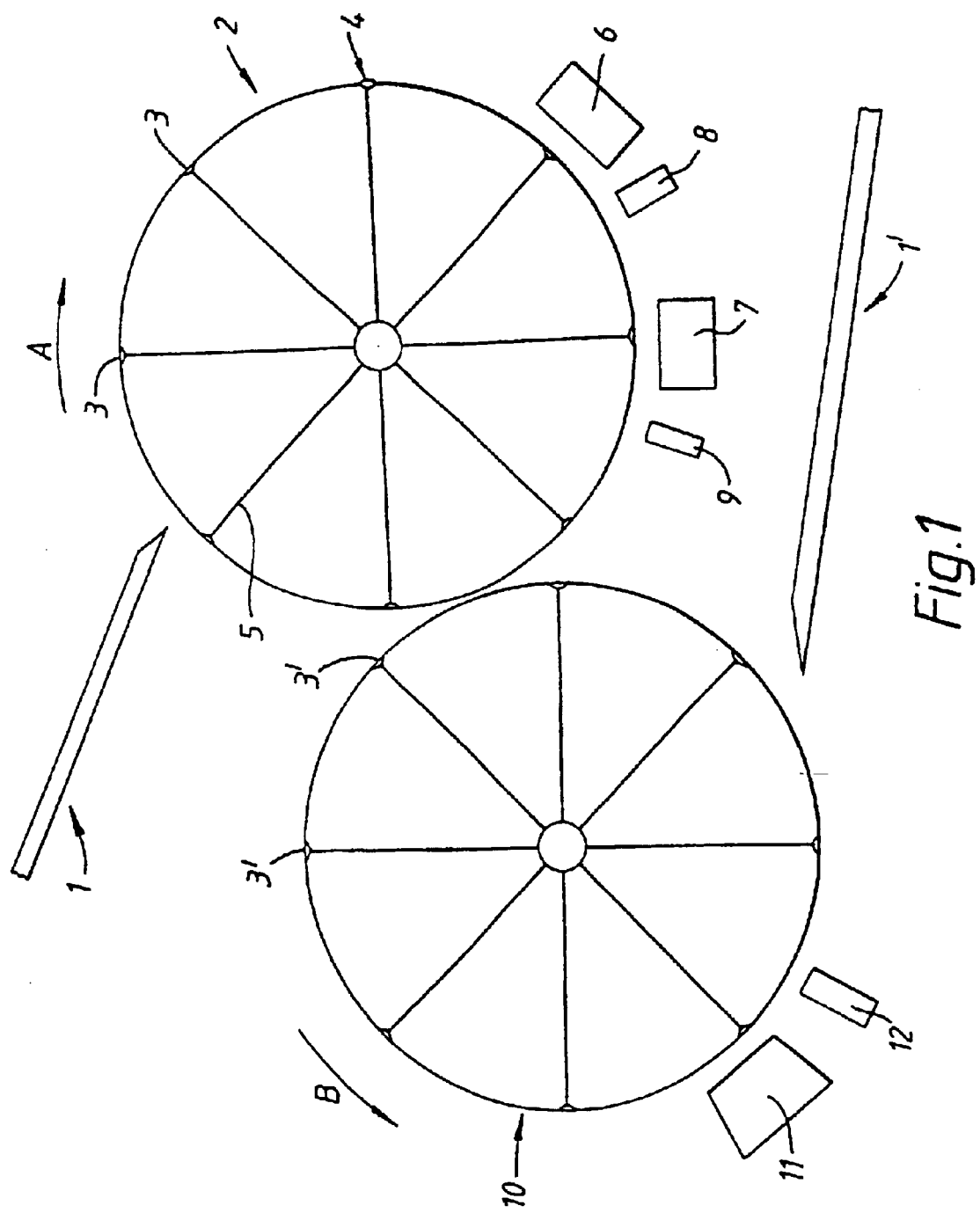
FIG. 1 shows schematically a side view of an apparatus for coating a tablet core.

The apparatus shown in FIG. 1 is for coating both faces of pharmaceutical tablet cores. The apparatus comprises an inclined tablet core feed chute 1 leading to a first rotatable wheel 2 having circular depressions 3 in its outer surface. The cores 4 are fed from the chute 1 into the depressions 3 where they are held by suction by means of a suction line 5 in communication with the base of the depression 3 via an opening. The first drum is rotated in the direction shown by the arrow A. Adjacent to the outer surface of the wheel 2 downstream from the feed chute 1 is an active coating station 6 and a cover coating station 7. Downstream from the active coating station is an active coating fusing station 8 at which the active coating is fused and downstream from the cover coating station 7 is a cover coating fusing station 9 at which the cover coating is fused. A cooling station (not shown) may be provided downstream from each of the fusing stations 8, 9 where cool air is directed at the core to cool the fused coating.

A second wheel 10 similar to the first wheel 2 is arranged adjacent to the first wheel 2, the nip between the wheels being downstream of the fusing station 9. The second wheel 10 rotates in an opposite sense to that of the first wheel 2 as shown by the arrow B. Arranged adjacent to the outer edge of the second wheel 10 downstream from the nip of the two wheels are a second cover coating station 11 and a second fusing station 12.

Figure 2:
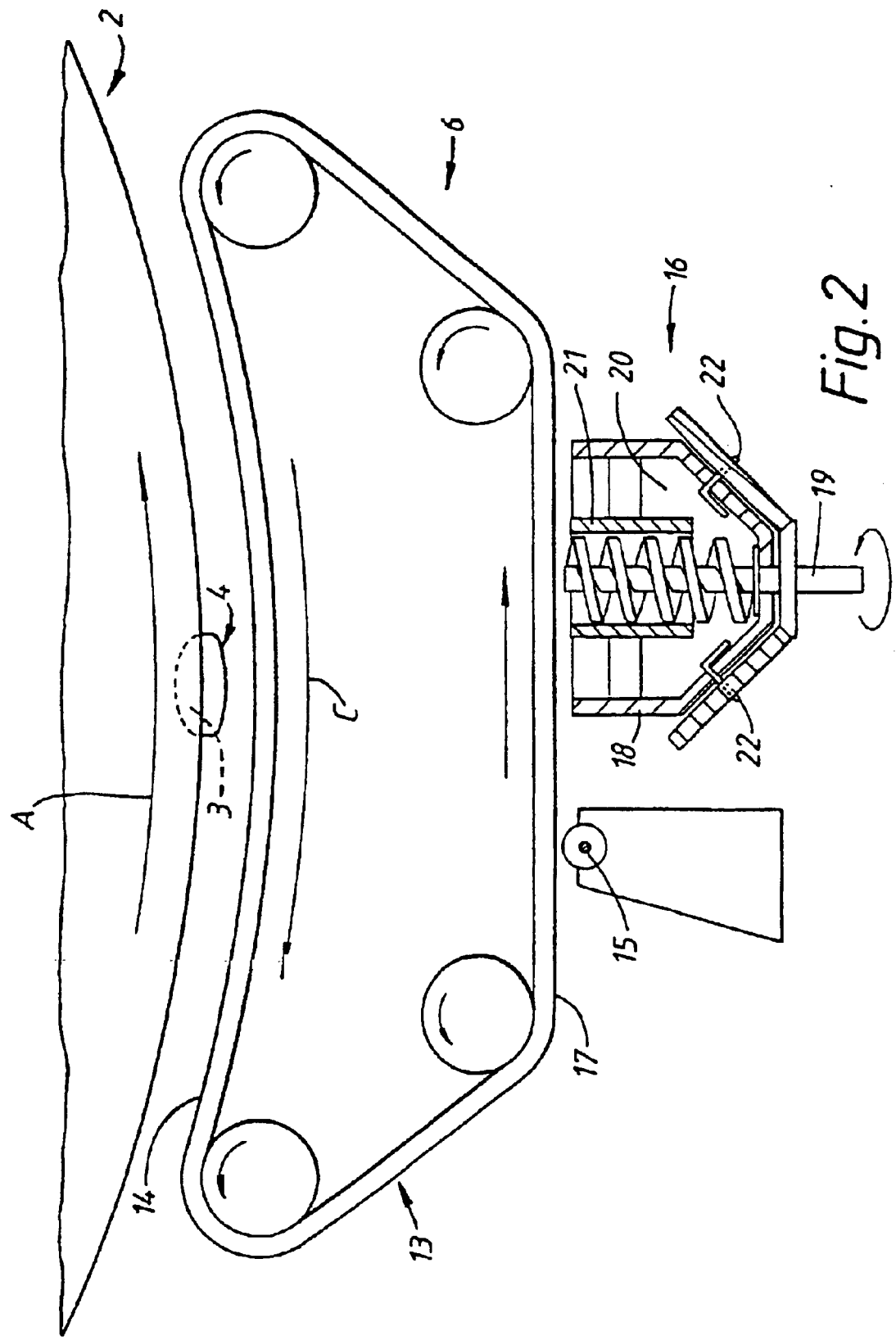
FIG. 2 shows schematically a side view of a part of the apparatus of FIG. 1.

FIG. 2 shows the active coating device 6 in more detail. FIG. 2 shows a portion of the wheel 2 together with a core 4 in a depression 3 on the surface of the wheel 2. As described below, the apparatus of FIG. 2 can be used to form wafers of coating material in accordance with the present invention.

The active coating station 6 comprises a conveyor 13 arranged in a loop in a vertical plane so that the upper surface 14 faces the surface of the wheel and the cores 4 which pass the device 6 as the wheel rotates. The contour of the upper surface 14 of the conveyor 13 is chosen to match the contour of the outer surface of the wheel so that the distance between the core and the upper surface of the conveyor is unchanged as the wheel rotates. The direction of rotation C of the conveyor 13 is such that the direction of movement of the upper surface of the conveyor is opposite to that of the movement of the core over the upper surface of the conveyor. Alternatively, the direction of movement of the upper surface of the conveyor and the core may be the same.

As shown in FIG. 2, a corona charge wire 15 and powder source 16 are arranged beneath the conveyor immediately below the lower surface 17 of the conveyor.

The corona charge wire 15 sprays charge onto the lower surface 17 of the conveyor. It will be appreciated that a different method could be used to apply charge to the conveyor.

The powder source 16 uses an archimedes screw to form a small mound of powder beneath the lower surface of the conveyor. The source 16 comprises a hopper 18 containing the powder including the biologically active component, and an Archimedes screw 19 which in use passes through the powder material 20 in the hopper 18 and through a vertical barrel 21. Thus, the powder material 20 is circulated from the lower regions of the hopper 18 to the top of the barrel 21 where a moving heap of powder is formed. The heap will be of substantially constant size and shape as excess powder overflows from the top of the barrel 21 and is returned to the hopper 18.

Stirrers 22 are provided in the hopper 18 to help to improve the flow of the powder and break up any agglomerates.

Thus a small moving heap of powder of substantially constant size and shape is formed beneath the lower surface of the conveyor 17.

It will be appreciated that a device other than the Archimedes screw could be used to form the heap of powder.

The powder source 16 is located downstream from the charge spraying device 15 and powder from the heap of powder is attracted to the surface of the charged conveyor 17 where it forms a thin, uniform layer which is transported to the upper surface 14 of the conveyor.

The tablet core 4 passing over the upper surface of the conveyor is held at a different potential from that of the conveyor 13, either by earthing the core or applying a charge to the core, and powder on the conveyor moves from the conveyor to the exposed surfaces of the tablet care 4 to form a powder coating.

The active coating station 6 is enclosed in a housing (not shown) to reduce the risk of powder loss of the active powder. In use the housing has an opening above the upper surface of the conveyor 14 so that the tablet core 4 is exposed to the active powder coating material as it passes the station 6.

It will be appreciated that the thickness of the powder layer formed on the surface of the tablet core depends on several factors including the amount of charge sprayed onto the conveyor, the magnitude of the charge applied to the core, the size of the heap of powder produced, the size of the opening in the housing and the speed of the conveyor. Those factors will be varied to give the desired coating depending on the type of powder and core used.

The composition of the active coating material used will of course depend on the active ingredient to be used and the amount of the coating to be applied.

Active materials most suitable to be applied to the tablet include those materials having a high therapeutic activity, for example those where the usual prescribed dose is about 1 mg or less, and which have a good stability to degradation due to heat where the coating material containing active material is to be heated.

An active material which may be applied to a tablet core in accordance with the invention is Diltiazem HCL.

The amount of active ingredient to be coated onto each core or other substrate will generally be small and the active ingredient will usually be diluted with one or more excipients. The excipients used will be chosen so that they aid the coating of the active material onto the cores by, for example improving the electrostatic properties of the powder and its physical properties and aiding the formation of the fused active coating, for example the excipient may be a material which melts at a low temperature to aid the formation of a film.

Where the active coating material is a powder, the particle size will be an important factor with regard to the transfer of the active coating material from the conveyor to the tablet core and to the subsequent fusing of the material. Usually a particle size range of 1 to 200 $\mu$m will be used (at least 90% of the particles of the powder having a size within that range).

One example of an active coating material is as follows:

| | |
|---|---|
| Xylitol | 45% wt |
| Diltiazem HCL (active) | 45% wt |
| TiO$_2$ | 9% wt |
| Colloidal silica | 1% wt |

It is thought that in at least one embodiment of the invention, the active composition will comprise three main components together with additives.

The components may, for example, comprise the following
i) a continuous phase component, for example Xylitol or PEG 6000,
ii) the active component,
iii) a particle seed and/or charge modifying component, for example TiO$_2$ or silica,
iv) a flow aid, for example colloidal silica or magnesium stearate.

Each component may comprise one or more different materials.

The active coating material of the above example was in the form of a powder and had a particle size distribution such that at least 90% wt of the particles had a size in the range of from 5 to 25 µm.

It is often preferred that at least 90% by weight of the particles have a size in the range of from 1 to 45 µm. In one preferred embodiment 90% by weight of the particles have a size less than 70 µm, 50% by weight have a size less than 40 µm and 10 by weight of the particles have a size less than 10 µm.

The active powder coating material may be produced using one or a combination of the following processing steps:
a) precipitation of two or more of the components to form composite particles
b) spray drying of two or more of the components to form composite particles
c) granulation
d) extrusion
e) micronisation.

For example, all of the components of the composition may be co-micronised to give a powder material having the desired particle size.

An example of a powder cover coating material is as follows:

| | |
|---|---|
| 39.75% | Eudragit RS (ammoniomethacrylate copolymer) |
| 39.75% | Klucel (hydroxy propyl cellulose) |
| 15.0% | Titanium dioxide Aluminium lake |
| 0.5% | Aerosil 200 (colloidal silicon dioxide) |

The cover coating material was prepared by the following method:
a) A sample containing the % wt of components listed above was premixed in a high shear mixer. Water was added to the mixture in a high shear mixer for a few minutes to give a granulated mixture which was dried in a fluid bed drier at a temperature of about 45° C. for 20 to 30 minutes to give a material having a moisture content (measured as loss on drying) below 3% by weight. The material was impact milled and then micronised using a fluid energy mill to a powder containing particles having a size distribution such that 50% by volume of particles were of a size less than 20 µm.

The cover coating material will usually include components to control the dissolution rate of the cover coating to give controlled release of the active material in the active coating layer. Where more than one active coating is applied to each tablet or substrate, the release of each active coating can be different where different materials are used for the cover coating over each of those active coatings.

Where one or more of the coatings are applied as liquid coatings, a suitable liquid coating device would be used at the active coating station 6 and/or the cover coating station 7 and the fusing device would be replaced by, for example a drying device to dry the liquid coating, if necessary.

In an embodiment of the invention an apparatus similar to that shown in FIG. 2 is used to form wafers of coating material.

The apparatus comprises a conveyor belt of chemically inert material having a Teflon (RTM) coating. A corona charge wire is arranged immediately below the lower surface of the conveyor and sprays charge onto the lower surface. A powder source similar to that shown in FIG. 2 is also arranged beneath the lower surface of the conveyor downstream of the corona wire. The powder material in the powder source contains an active component and may have similar composition to the active powder described above. Preferably a higher proportion of film forming components are added to the powder, for example hydroxypropylcellulose (HPC).

An example of an active coating material is as follows:
Eudragit RS 23%
Diltiazem HCL (active) 40%
HPC 25%
TiO$_2$ 7%
PEG 4000 5%

The amounts of the components are expressed as percent by weight.

Powder from the powder source is attracted to the surface of the charged conveyor where it forms a thin, uniform layer of powder on a part of the outer surface of the conveyor belt. A heater is positioned downstream of the powder source and the heater fuses the powder material on the conveyor surface to form a fused film coating on the surface. The film coating is conveyed on the conveyor to a region where it is removed as a thin strip of film.

A cooling station may be positioned downstream of the heater to cool the film coating. The film strip removed from the conveyor may be passed to a cutting station where it is divided into portions, each of which may contain a dose of active material.

In an alternative embodiment of the invention, powder material is deposited onto a tape, preferably of plastics material.

In a further embodiment of the invention, the active coating is applied as a liquid. A head for applying the liquid is positioned such that the outlet or outlets of the head is less than 1 mm from the surface to which the material is to be applied.

The head may be an ink jet printer head, for example an adapted Compact 200 head manufactured by Alphadot Limited. That head has 5 outlets spread over an area of about 10 mm and can be used to direct liquid coating material towards the exposed surfaces of the substrate.

The liquid coating material comprises the active component and a solvent, preferably water, and an excipient, for example PEG, to aid in film forming. Preferably the solids content of the liquid coating material is very low, advantageously there would be substantially no solids content and advantageously the active material is fully dissolved in the solvent.

While it is envisaged that where the active layer is applied using an ink jet printer head, the active material might be applied directly to a substrate from which it can be removed, it is thought that, in particular where the active material is to be peelable from the substrate in the form of a wafer, the active material would be applied to a base layer which is removable from the substrate.

For example, a first base coating layer would be applied to a substrate using the apparatus shown in FIG. 2. Where the base coating material is applied to the substrate in the form of a powder material, the base coating would usually be fused to form the base coating layer. The base coating layer would be peelable from the substrate. One or more regions of active coating material would be applied to the base coating layer, for example using an ink jet printer head.

A cover coating would be applied over the active coating material. Where the cover coating is in the form of a powder, the cover coating would usually be fused to form the cover coating layer. The material would be removed from the substrate in the form of a three-layer wafer in which the active material was sandwiched between two layers. The wafer may subsequently be divided into smaller portions.

In a further embodiment of the invention, the active coating material is applied to a substrate using an ultrasonic spray head. The ultrasonic spray head forms a cloud of liquid droplets which are charged electrostatically. A charge may be imparted on the droplets, for example, by applying a high voltage to the ultrasonic spray head. The charged droplets become attracted to the substrate which is at a potential difference from the droplets.

Examples of active liquid coating materials which may be used are as follows

| | | |
|---|---|---|
| a) | Sodium citrate | 0.02 |
| | Chlorpheniramine maleate | 2.48 |
| | Propylene glycol | 4.00 |
| | Water | 18.50 |
| | Ethanol | 75.00 |
| b) | Sodium citrate | 0.02 |
| | Chlorpheniramine maleate | 2.00 |
| | Methocel E15 | 1.00 |
| | Lactose B.P. | 6.00 |
| | PEG 4000 | 1.00 |
| | Water | 89.98 |

The amounts given above represent percentage by weight of each component.

The apparatus may include heating means (not shown) for drying the applied coating material. However, where the liquid coating material is such that the solvent evaporates quickly, the heater may not be required. It will be appreciated that where the heater is used the temperature required to dry the active coating will be significantly lower than the temperature required to fuse powder coating material as described above.

Figure 3:
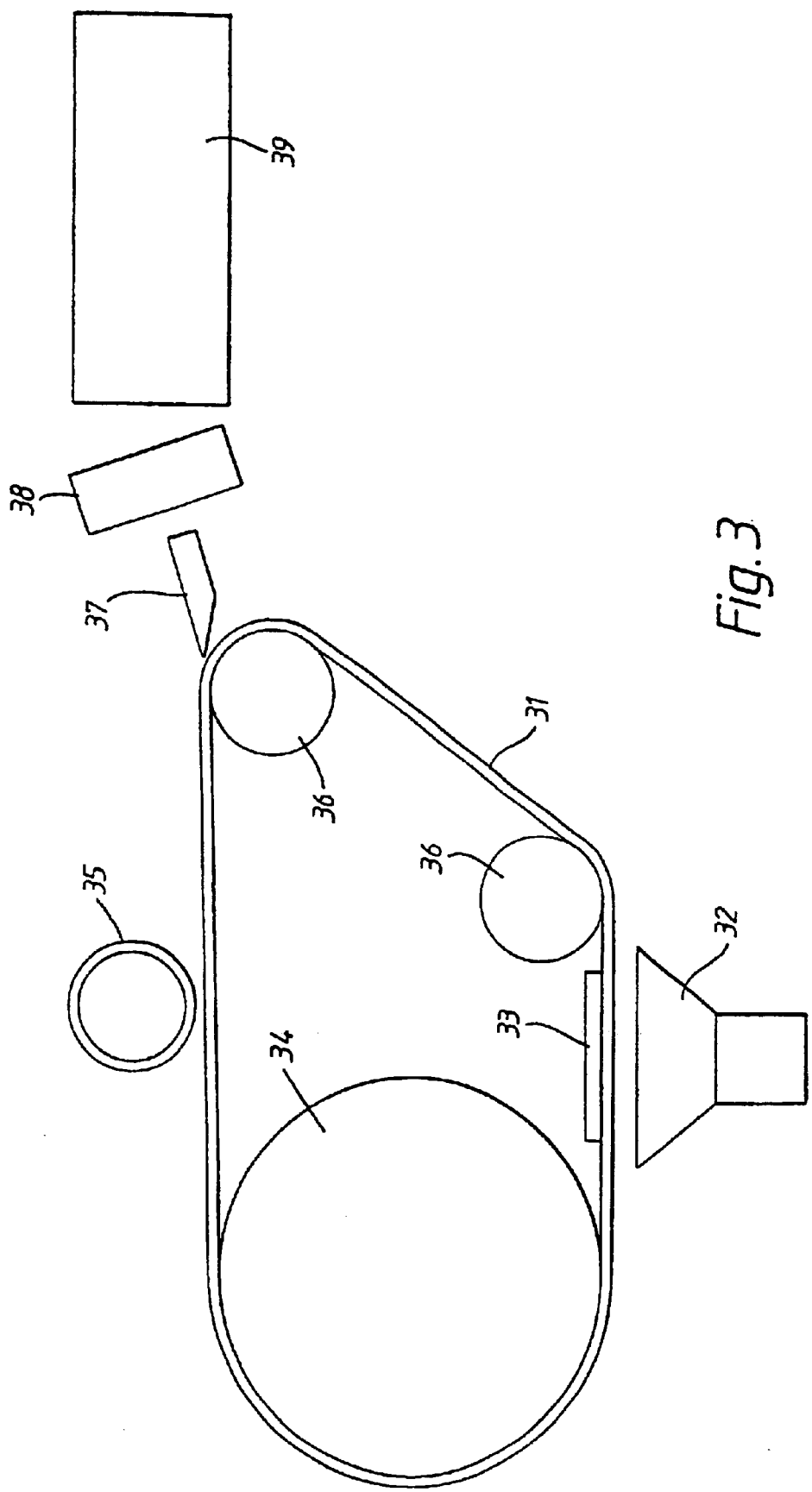
FIG. 3 shows schematically a side view of an apparatus for coating a substrate in accordance with the invention.

FIG. 3 shows a further embodiment of the invention.

FIG. 3 shows a schematic view of an alternative arrangement of the apparatus for producing wafers including active material.

The apparatus is similar in operation to that described above in respect of FIG. 2 and comprises a stainless steel conveyor belt 31 (which may be coated with PTFE on its external surface) mounted for rotation on three rollers 34, 36. A powder hopper 32 is arranged below the conveyor 31 and wafer forming powder material is loaded into the hopper. The hopper is arranged to produce a recirculating powder bed either by fluidising the powder in the hopper with dry air or by using an auger feed screw arrangement in the hopper and vibrating the powder in the hopper.

The hopper 32 is charged to from 0.5 to 10 kV either positively or negatively depending on the wafer forming powder composition to be used. For the two compositions given below, the hopper would be charged negatively.

A plate 33 is arranged above the portion of the conveyor belt 31 which is adjacent to the hopper 32. The plate may be a stainless steel plate and is charged to a potential difference from that of the hopper 32. The plate will normally be charged to the opposite sign to that of the hopper. The charge on the plate 33 may be from 0.1 to 10 kV depending on the powder composition used and the thickness of the wafer to be formed.

The thickness of the layer formed on the surface of the belt will usually be from 0.5 to 3 mm. The charge applied to the hopper and to the plate 33, and the speed of the belt will be chosen to give the desired thickness.

The powder composition is attracted to the conveyor belt 31 and adheres to the exterior surface of the belt to form a powder layer. The size of the hopper will usually be chosen so that the whole width of the conveyor belt is coated with powder. It is envisaged, however, that the powder might coat less than the whole width of the conveyor belt 31. Also, the hopper 32 may comprise a group of several hoppers each for supplying the same or different powder compositions to the conveyor belt 31. Thus the wafer produced using the apparatus may be a composite wafer in that it includes portions having different compositions. For example, the wafer might comprise a first layer including active material and a second coating layer including no active material.

As indicated above, the wafer might comprise a first layer including no active material, a second layer including active material and a third layer including no active material. That arrangement is particularly preferred because the active material is sandwiched between two outer layers which help to protect the active material from mechanical or chemical damage.

Such a wafer may be formed by applying a coating layer to a substrate, applying the active material to the coating layer to form an active layer and subsequently applying a cover coating layer over the active layer. The first coating layer is removable from the substrate so that a three-layer wafer is formed.

Where reference is made herein to the active material being applied to a substrate and being removable from a substrate, it will be understood that that includes the case in which the active material is applied to a coating layer which has previously been applied to the substrate, the active coating layer being removable from the substrate together with the coating layer.

The coated portion of the conveyor belt travels from the region of the hopper to the heated roller 34. The heated roller 34 is heated to slightly above the melting point of the powder composition on the surface of the conveyor belt. As the conveyor belt moves around the heated roller 34, the powder composition on the outer 320 surface of the conveyor belt melts and forms a fused coating on the surface of the belt.

A chilled roller 35 is arranged above the conveyor belt 31 downstream from the heated roller 34. The fused coating layer on the surface of the conveyor belt passes under the chilled roller 35 which smoothes the upper surface of the coating layer and cools the coatings so that it solidifies to form a wafer on the exterior surface of the conveyor belt. It will be appreciated that other methods could be used to cool and smooth the coating layer, for example cool air jets arranged above the conveyor belt downstream from the heated roller 34.

The solidified wafer is transported on the conveyor belt 31 to the doctor blade 37 where the wafer is peeled from the surface of the belt. The conveyor belt continues around the guide rollers 36 and a further coating is deposited onto the conveyor belt as powder material moves from the hopper to the belt as described above. Thus the apparatus can be used to produce a continuous wafer.

It is thought that the width of the conveyor belt would usually be up to 50 cm. The material may be applied across the whole width of the conveyor belt. Alternatively, the material might be applied as several bands of material across the belt, the material being supplied from several separate hoppers arranged below the belt.

The wafer peeled from the conveyor passes to a cutter 38 which may be a rotary knife wafer chopper where the wafer is cut into uniform pieces. The cut wafer portions may be of any shape or size but will usually contain one dose of the active material present in the wafer. It will be appreciated that while circular or eliptical shaped wafer portions may be preferred from an aesthetic point of view, such shapes would lead to greater wastage of wafer material than, for example, rectangular-shaped wafer portions.

The pieces are then passed to a packaging station 39 where they are packaged using conventional methods to form, for example, blister packs or plasters for use as a patch on the skin.

Examples of suitable coating compositions are given above. Particularly suitable powder compositions for use with the apparatus are as follows:

| | |
|---|---|
| Diltiazem HCl (active) | 50% |
| Eudragit RSPO Type C (ammoniomethacrylate copolymer) | 47.5% |
| Titanium dioxide | 2% |
| Sunset yellow pigment | 0.5% |

The % given are % by weight. The components were mixed and the mixture was extruded and micronised to give a powder having a narrow particle size distribution below 150 $\mu$m. For example, the particle size distribution may be as follows:

| |
|---|
| 10% by weight less that 20 $\mu$m |
| 50% by weight less than 50 $\mu$m |
| 90% by weight less than 90 $\mu$m. |

Composition 2

| | |
|---|---|
| Diltiazem HCl | 40% |
| Polyethylene glycol 6000 | 30% |
| Xylitol | 20% |
| Titanium dioxide | 10% |

The components were wet granulated together, milled and sieved to form a powder having a narrow particle size distribution between 75 $\mu$m and 20 $\mu$m.

It will be understood that other compositions containing active material could be used. The composition will usually include from 1% to 90% by weight of active material based on the weight of the composition. The remainder of the formulation will usually comprise a polymeric matrix of binder material, for example Eudragit E100, gelatine, PVA, PVP-PVA, PEG, lactitol, polypropylene. The compositions may additionally include plasticisers, opacifiers, disintegrants, detacifiers and/or pigments.

The apparatus described above may be modified so that the powder composition is deposited on a tape of material which is fed around the apparatus on the exterior surface of the conveyor, the tape having a wafer coating being removed from the apparatus. The tape may be inedible, in which case the coating material may be removed from the tape on administration, where the active material is to be administered orally. Alternatively, the tape may be used, for example, as a patch. Where the tape is edible, the active material may be administered without removal from the tape, for example the tape and wafer portion may be swallowed together.

Furthermore, as indicated above, the coating composition may be applied to the substrate using a different method to that described above. For example, the coating material may be applied in the form of a liquid using a head similar to that used in ink-jet printing. Alternatively, the coating material may be applied in the form of a liquid using an ultrasonic spray head. Dots of coating composition would be applied to regions of the substrate using the head.

What is claimed is:

1. A method of coating substrate which is a belt sheet, film, or tape, the method comprising the step of preparing a pharmaceutical product by applying an active coating material to the substrate to form an active coating layer, the active coating material comprising biologically active material, wherein the active coating material is applied electrostatically as a powder, and, after the active coating material is applied, the active coating material is fused to form an active film layer, wherein the active coating material is removable from the substrate as a wafer comprising the active film layer, and wherein the active coating layer is divided into portions.

2. The method according to claim 1, which further includes the step of removing the portions of active coating layer from the substrate as wafers comprising the active film layer.

3. The method according to claim 1, wherein the substrate is pre-coated with one or more coating layers removable from the substrate and the active coating layer is removable therewith.

4. The method according to claim 1, which includes the step of applying a cover coating material onto the active coating layer to form a cover coating layer wherein the active coating layer is substantially completely covered by the cover coating layer, and wherein the cover coating layer is removable from the substrate.

5. The method according to claim 4, wherein the cover coating material is applied electrostatically as a powder and after application is fused to form a cover film coating.

6. The method according to claim 4, wherein the cover coating layer is removable with the active coating layer.

7. The method according to claim 4, wherein the cover coating material includes biologically active material.

8. The method according to claim 4, wherein the method further includes the step of applying a further coating material to a surface of the substrate to form a further coating layer wherein the further coating layer is removable from the substrate.

9. The method according to claim 8, wherein the further coating material includes biologically active material, the further coating layer forming a further active coating layer and the method further includes the step of applying a further cover coating material onto the further active coating layer to form a further cover coating layer wherein the further active coating layer is substantially completely covered by the further cover coating layer and wherein the further cover coating layer is removable from the substrate.

10. The method according to claim 9, wherein the active material of the active coating layer and the further active coating layer are the same.

11. The method according to claim 4, wherein the method includes the step of applying a second active coating layer onto a surface of the substrate, the second active coating layer forming a second active coating region on the surface of the substrate, the second active coating layer being removable from the substrate, and applying a second cover coating layer onto the second active coating layer to form a second cover coating layer wherein the second active coating layer is substantially completely covered by the second cover coating layer, the second cover coating layer being substantially separate from the first cover coating layer, and being removable from the substrate.

12. The method according to claim 1, which comprises applying to the substrate a base coating layer, applying the active coating material to the base coating layer and applying a cover coating layer over the active coating layer, the three layers being removable together by peeling from the substrate in the form of a three-layer wafer.

13. The method according to claim 12, wherein the base coating layer and the cover coating layer are each applied electrostatically as a powder and each fused to form a film.

14. The method according to claim 1 wherein at least 90% by weight of the particles of the active coating material have a particle size in the range of from 1 to 45 microns.

15. The method according to claim 1 wherein 90% by weight of the particles have a size less than 70 microns, 50% by weight have a size less than 40 microns and 10% by weight have a size less than 10 microns.

16. The method according to claim 1 wherein the method comprises supporting the substrate adjacent to the source of the active coating material with a surface of the substrate maintained at such a different electric potential from that of the active coating material that the application of the electric potential causes the active coating material to move from the source of the active coating material towards the substrate, a surface of the substrate becoming coated with the active coating material.

17. The method according to claim 1 wherein the substrate is supported from above and the powder moves from the source upwards towards a lower surface of the substrate.

18. The method according to claim 1 wherein each portion into which the active coating layer is divided contains substantially one dose of the active material.

19. The method according to claim 1 wherein the active coating material is applied to a plurality of individual regions on the surface of the substrate.

20. A method of coating a substrate which is a belt, sheet, film, or tape, the method comprising the step of preparing a pharmaceutical product by applying one or more coating layers to the substrate, the layer or the first layer being applied directly to a surface of the substrate, the layer or at least one of the layers comprising active coating material, the active coating material comprising biologically active material, wherein the active coating material is applied electrostatically as a powder and after the active coating material is applied the active coating material is fused to form an active film layer, wherein the layer or layers applied are removable from the substrate as a coherent layer or layers, and wherein the layer or layers applied are divided into portions.

21. The method according to claim 20, which further includes the step of removing portions of said layer or layers from the substrate as wafers comprising the active film layer.

22. The method according to claim 20, wherein the substrate is coated with one or more coating layers removable from the substrate before application of the active coating layer and the active coating layer is removable therewith.

23. The method according to claim 20, which includes the step of applying a cover coating material onto the active coating layer to form a cover coating layer wherein the active coating layer is substantially completely covered by the cover coating layer, and wherein that cover coating layer is removable from the substrate.

24. The method according to claim 23, wherein the cover coating material is applied electrostatically as a powder and after application is fused to form a cover film coating.

25. The method according to claim 23, wherein the cover coating layer is removable with the active coating layer.

26. The method according to claim 23, wherein the cover coating material includes biologically active material.

27. The method according to claim 23, wherein the method further includes the step of applying a further coating material to a surface of the substrate to form a further coating layer wherein the further coating layer is removable from the substrate.

28. The method according to claim 27, wherein the further coating material includes biologically active material, the further coating layer forming a further active coating layer and the method further includes the step of applying a further cover coating material onto the further active coating layer to form a further cover coating layer wherein the further active coating layer is substantially completely covered by the further cover coating layer and wherein the further cover coating layer is removable from the substrate.

29. The method according to claim 28, wherein the active material of the active coating layer and the further active coating layer are the same.

30. The method according to claim 23, wherein the method includes the step of applying a second active coating layer onto a surface of the substrate, the second active coating layer forming a second active coating region on the surface of the substrate, the second active coating layer being removable from the substrate, and applying a second cover coating layer onto the second active coating layer to form a second cover coating layer wherein the second active coating layer is substantially completely covered by the second cover coating layer, the second cover coating layer being substantially separate from the first cover coating layer, and being removable from the substrate.

31. The method according to claim 20, which comprises applying to the substrate a base coating layer, applying the active coating material to the base coating layer and applying a cover coating layer over the active coating layer, the three layers being removable together by peeling from the substrate in the form of a three-layer wafer.

32. The method according to claim 31, wherein the base coating layer and the cover coating layer are each applied electrostatically as a powder and each fused to form a film.

33. The method according to claim 20, wherein at least 90% by weight of the particles of the active coating material have a particle size in the range of from 1 to 45 microns.

34. The method according to claim 20, wherein 90% by weight of the particles have a size less than 70 microns, 50% by weight have a size less than 40 microns and 10% by weight have a size less than 10 microns.

35. The method according to claim 20, wherein the method comprises supporting the substrate adjacent to source of the active coating material with a surface of the substrate maintained at such a different electric potential from that of the active coating material that the application of the electric potential causes the active coating material to move from the source of the active coating material towards the substrate, a surface of the substrate becoming coated with the active coating material.

36. The method according to claim 20, wherein the substrate is supported from above and the powder moves from the source upwards towards a lower surface of the substrate.

37. The method according to claim 20, wherein each portion into which said layer or layers are divided contains substantially one dose of the active material.

38. The method according to claim 20, wherein the active coating material is applied to a plurality of individual regions on the surface of the substrate.

39. A method of coating a substrate using a coating apparatus having a conveying surface, the method comprising the steps of preparing a pharmaceutical product by applying an active coating material to the substrate to form an active coating layer, said substrate being the conveying surface of the coating apparatus, the active coating material comprising biologically active material, wherein the active coating material is applied electrostatically as a powder, and, after the active coating material is applied, the active coating material is fused to form an active film layer, and wherein the active coating material is removable from the substrate as a wafer comprising the active film layer, and wherein the active material is removed as a wafer comprising the active film layer and divided into portions.

40. The method according to claim 39, wherein the active coating material is applied to a conveyor belt.

41. The method according to claim 39, wherein the substrate is pre-coated with one or more coating layers removable from the substrate and the active coating layer is removable therewith.

42. The method according to claim 39, which further includes the step of applying a cover coating material onto the active coating layer to form a cover coating layer wherein the active coating layer is substantially completely covered by the cover coating layer, and wherein that cover coating layer is removable from the substrate, wherein the cover coating material is applied electrostatically as a powder and after application is fused to form a cover film coating.

43. The method according to claim 42, wherein the cover coating layer is removable with the active coating layer.

44. The method according to claim 42, wherein the cover coating material includes biologically active material.

45. The method according to claim 42, wherein the method further includes the step of applying a further coating material to a surface of the substrate to form a further coating layer wherein the further coating layer is removable from the substrate.

46. The method according to claim 45, wherein the method includes the step of applying a second active coating layer onto a surface of the substrate, the second active coating layer forming a second active coating region on the surface of the substrate, the second active coating layer being removable from the substrate, and applying a second cover coating layer onto the second active coating layer to form a second cover coating layer wherein the second active coating layer is substantially completely covered by the second cover coating layer, the second cover coating layer being substantially separate from the first cover coating layer, and being removable from the substrate.

47. The method according to claim 39, which comprises applying to the substrate a base coating layer, applying the active material to the base layer and applying a cover coating layer over the active coating layer, the three layers being removable together by peeling from the substrate in the form of a three-layer wafer.

48. The method according to claim 47, wherein the base coating layer and the cover coating layer are each applied electrostatically as a powder and each fused to form a film.

49. The method according to claim 39, wherein at least 90% by weight of the particles of the active coating material have a particle size in the range of from 1 to 45 microns.

50. The method according to claim 39, wherein 90% by weight of the particles have a size less than 70 microns, 50% by weight have a size less than 40 microns and 10% by weight have a size less than 10 microns.

51. The method according to claim 39, wherein each portion into which the active coating applied to the substrate is divided contains substantially one dose of the active material.

52. The method according to claim 39, wherein the portions divided from the wafer constitute individual solid dosage form.

53. The method according to claim 39, wherein the active coating material is applied to a plurality of individual regions on the surface of the substrate.

54. A method of coating a substrate using a coating apparatus having a conveying surface, the method comprising of the steps of preparing a pharmaceutical product by applying one or more coating layers to the substrate, the layer or the first layer being applied directly to a surface of the substrate, the layer or at least one of the layers comprising active coating material, said substrate being the conveying surface of the coating apparatus, the active coating material comprising biologically active material, wherein the active coating material is applied electrostatically as a powder, and wherein after the active coating material is applied the active coating material is fused to form an active film layer, and wherein the layer or layers applied are removable from the substrate as a coherent layer or layers, and wherein the active coating is removed from the substrate as a coherent layer or layers and the layer or layers are divided into portions.

55. The method according to claim 54, wherein the active coating material is applied to a conveyor belt.

56. The method according to claim 54, which further includes the step of applying a cover coating material onto the active coating layer to form a cover coating layer wherein the active coating layer is substantially completely covered by the cover coating layer, and wherein that cover coating layer is removable from the substrate, and wherein the cover coating material is applied electrostatically as a powder and after application is fused to form a cover film coating.

57. The method according to claim 56, wherein the method includes the step of applying a second active coating layer onto a surface of the substrate, the second active coating layer forming a second active coating region on the surface of the substrate, the second active coating layer being removable from the substrate, and applying a second cover coating layer onto the second active coating layer to form a second cover coating layer wherein the second active coating layer is substantially completely covered by the second cover coating layer, the second cover coating layer being substantially separate from the first cover coating layer, and being removable from the substrate.

58. The method according to claim 56, which comprises applying to the substrate a base coating layer, applying the active material to the base layer and applying a cover coating layer over the active coating layer, the three layers being removable together by peeling from the substrate in the form of a three-layer wafer.

59. The method according to claim 58, wherein the base coating layer and the cover coating layer are each applied as a powder and each fused to form a film.

60. The method according to claim 59, wherein at least 90% by weight of the particles of the active coating material have a particle size in the range of from 1 to 45 microns.

61. The method according to claim 54, wherein 90% by weight of the particles have a size less than 70 microns, 50% by weight have a size less than 40 microns and 10% by weight have a size less than 10 microns.

62. The method according to claim 54, wherein each portion into which said layer or layers are divided contains substantially one dose of the active material.

63. The method according to claim 54, wherein the portions into which said layer or layers are divided constitute wafer solid dosage forms.

64. The method according to claim 54, wherein the active coating material is applied to a plurality of individual regions on the surface of the substrate.

65. A method of coating a plurality of coating regions onto the surface of a substrate which is a belt, sheet, film, or tape, the method comprising the step of preparing a pharmaceutical product by:
(a) applying an active coating material to the substrate to form a plurality of active coating regions comprising active coating layers, the active coating material comprising biologically active material and being applied electrostatically as a powder wherein after the active coating material is applied the active coating material is fused to form regions of active film coating,
(b) applying a cover coating material to a surface of the substrate to form a plurality of cover coating regions, the cover coating regions forming layers of cover coating material, each active coating region being substantially completely covered by a cover coating region, wherein each region of active coating and cover coating is removable from the substrate as a wafer comprising the active film coating and the cover coating, and
(c) dividing to form individual dosage units.

66. The method according to claim 65, wherein the cover coating material is applied electrostatically as a powder and after application is fused to form regions of cover film coating.

67. The method according to claim 65, the method including the step of removing the portions of active coating regions from the substrate to form wafers comprising active material.

68. The method according to claim 65, wherein at least 90% by weight of the particles of the active coating material have a particle size in the range of from 1 to 45 microns.

69. The method according to claim 65, wherein 90% by weight of the particles have a size less than 70 microns, 50% by weight have a size less than 40 microns and 10% by weight have a size less than 10 microns.

70. A method of coating a plurality of coating regions onto the surface of a substrate using a coating apparatus having a conveying surface, the method comprising the steps of preparing a pharmaceutical product by:
(a) applying an active coating material to the substrate to form a plurality of active coating regions comprising active coating layers, said substrate being the conveying surface of the coating apparatus, the active coating material comprising biologically active material and being applied electrostatically as a powder wherein after the active coating material is applied the active coating material is fused to form regions of active film coating,
(b) applying a cover coating material to a surface of the substrate to form a plurality of cover coating regions, the cover coating regions forming layers of cover coating material, each active coating region being substantially completely covered by a cover coating region, wherein each region of active coating and cover coating is removable from the surface of the substrate as a wafer comprising the active film coating and the cover coating, and wherein the active coating regions are removed as wafers each comprising the active film coating the cover coating, and divided into portions.

71. The method according to claim 70, wherein the cover coating material is applied electrostatically as a powder and after application is fused to form regions of cover film coating.

72. The method according to claim 70, wherein the active coating material is applied to a convey or belt.

73. The method according to claim 70, wherein at least 90% by weight of the particles of the active coating material have a particle size in the range of from 1 to 45 microns.

74. The method according to claim 70, wherein 90% by weight of the particles have a size less than 70 microns, 50% by weight have a size less than 40 microns and 10% by weight have a size less than 10 microns.

75. A method of coating a substrate which is a belt, sheet, film, or tape, the method comprising the steps of preparing a pharmaceutical product by applying an active coating material to the substrate to form an active coating layer, the active coating material comprising biologically active material, wherein the active coating material is applied electrostatically as a powder, and, after the active coating material is applied, the active coating material is fused to form an active film layer, and wherein the active coating material is removable from the substrate as a wafer comprising the active film layer, and wherein the active coating layer is removed from the substrate as a wafer comprising the active film layer and divided into smaller portions.

76. The method according to claim 75, wherein active coating material is applied to a plurality of individual regions on the surface of the substrate.

77. The method according to claim 76, wherein the amount of active coating material deposited on a given area of the substrate is controlled such that the product can subsequently be divided into portions with each portion containing a pre-determined amount of active coating material, each pre-determined amount being one dose of the active material.

78. The method according to claim 75, wherein the substrate is pre-coated with one or more coating layers removable from the substrate and the active coating layer is removable therewith.

79. The method according to claim 75, which includes the step of applying a cover coating material onto the active coating layer to form a cover coating layer wherein the active coaling lager is substantially completely covered by the cover coating layer, and wherein the cover coating layer is removable from the substrate.

80. The method according to claim 79, wherein the coating material is applied electrostatically as a powder and after application is fused to form a cover film coating.

81. The method according to claim 79, wherein the cover coating layer is removable with the active coating layer.

82. The method according to claim 79, wherein the cover coating material includes biologically active material.

83. The method according to claim 79, wherein the method further includes the step of applying a further coating material to a surface of the substrate to form a further coating layer wherein the further coating layer is removable from the substrate.

84. The method according to claim 83, wherein the further coating material includes biologically active material, the further coating layer forming a further active coating layer and the method further includes the step of applying a further cover coating material onto the further active coating layer to form a further cover coating layer wherein the further active coating layer is substantially completely covered by the further cover coating layer and wherein the further cover coating layer is removable from the substrate.

85. The method according to claim 84, wherein the active material of the active coating layer and the further active coating layer are the same.

86. The method according to claim 79, wherein the method includes the step of applying a second active coating layer onto a surface of the substrate, the second active coating layer forming a second active coating region on the surface of the substrate, the second active coating layer being removable from the substrate, and applying a second cover layer onto the second active coating layer to form a second cover coating layer wherein the second active coating layer is substantially completely covered by the second cover coating layer, the second cover coating layer being substantially separate from the first cover coating layer, and being removable from the substrate.

87. The method according to claim 79, which comprises applying to the substrate a base coating layer, applying the active material to the base coating layer and applying a cover coating layer over the active coating layer, the three layers being removable together by peeling from the substrate in the form of a three-layer wafer.

88. The method according to claim 87, wherein the base coating layer and the cover coating layer are each applied electrostatically as a powder and each fused to form a film.

89. The method according to claim 87, wherein at least 90% by weight of the particles of the active coating material have a particle size in the range of from 1 to 45 microns.

90. The method according to claim 87, wherein 90% by weight of the particles have a size less than 70 microns, 50% by weight have a size less than 40 microns and 10% by weight have a size less than 10 microns.

91. The method according to claim 87, wherein the method comprises supporting the substrate adjacent to the source of the active coating material with a surface of the substrate maintained at such a different electric potential from that of the active coating material that the application of the electric potential causes the active coating material to move from the source of the active coating material towards the substrate, a surface of the substrate becoming coated with the active coating material.

92. The method according to claim 87, wherein the substrate is supported from above and the powder moves from the source upwards towards a lower surface of the substrate.

93. The method according to claim 87, wherein each portion into which the active coating layer is divided contains substantially one dose of the active material.

94. The method according to claim 87, wherein the active coating material is applied to a plurality of individual regions on the surface of the substrate.

95. A method of coating a substrate using a coating apparatus having a conveying surface, the method comprising the steps of preparing a pharmaceutical product by applying an active coating material to the substrate to form an active coating layer, said substrate being the conveying surface of the coating apparatus, the active coating material comprising biologically active material, wherein the active coating material is applied electrostatically as a powder, and, after the active coating material is applied, the active coating material is fused to form an active film layer, and wherein the active coating material is removable from the substrate as a wafer comprising the active film layer, and wherein the active coating is removed as a wafer comprising the active film layer and divided to provide individual dosages of the active material.

96. A method of coating a substrate which is a belt, sheet, film, or tape, the method comprising the steps of preparing a pharmaceutical product by applying an active coating material to the substrate to form an active coating layer, the active coating material comprising biologically active material, wherein the active coating material is removable from the substrate as a wafer comprising the active coating layer, and the active coating material is applied electrostatically as a powder, and wherein active coating material is applied to a plurality of individual regions on the substrate, wherein after the active coating layer is applied the active coating material is fused to form an active film coating and wherein the amount of active coating material deposited on a given area of the substrate is controlled such that the product can subsequently be divided into portions with each portion containing a pre-determined amount of active coating material, each predetermined amount being one dose of the active material.

97. A method of coating a plurality of coating regions onto the surface of a belt of a coating apparatus, the method comprising the steps of preparing a pharmaceutical product by:
    (a) applying an active coating material to the belt to form a plurality of active coating regions comprising active coating layers, the active coating material comprising biologically active material and being applied electrostatically as a powder wherein after the active coating material is applied the active coating material is fused to form regions of active film coating,
    (b) applying a cover coating material to a surface of the belt to form a plurality of cover coating regions, the cover coating regions forming layers of cover coating material, each active coating region being substantially completely covered by a cover coating region, wherein each region of active coating and cover coating is removable from the belt as a wafer comprising the active film coating and the cover coating, and wherein the active coating regions are removed as wafers each comprising the active film coating the cover coating and divided into portions.

98. A method of coating a belt of a coating apparatus, the method comprising the steps of preparing a pharmaceutical product by applying an active coating material to the belt to form an active coating layer, the active coating material comprising biologically active material, wherein the active coating material is applied electrostatically as a powder, and, after the active coating material is applied, the active coating material is fused to form an active film layer, and wherein the active coating material is removable from the belt as a wafer comprising the active film layer, and wherein the active coating is removed as a wafer comprising the active film layer and divided into smaller portions.

99. A method of coating a substrate using a coating apparatus having a conveying surface, the method comprising the steps of preparing a pharmaceutical product by applying a base coat layer to the substrate, said substrate being said conveying surface of the coating apparatus;

applying an active coating material to the base coat layer to form an active coating layer, the active coating material comprising biologically active material; and applying a cover coating layer over the active coating layer, the three layers being removable together by peeling from the substrate in the form of a three-layer wafer, the base coat layer and the cover coating layer each being applied electrostatically as a powder and each being fused to form a film;

removing the active coating layer as said three-layer wafer comprising the active coating layer; and dividing to form individual dosage units.

100. A method of coating a substrate using a coating apparatus having a conveying surface, the method comprising the steps of preparing a pharmaceutical product by:

applying an active coating material to the substrate to form an active coating layer, said substrate being said conveying surface of the coating apparatus, the active coating material comprising biologically active material, wherein the active coating layer is removable from the substrate as a wafer comprising the active coating layer;

supporting the substrate adjacent to a source of the active coating material with a surface of the substrate being maintained at such a different electric potential from that of the active coating material that the application of the electric potential causes the active coating material to move from the source of the active coating material towards the substrate, whereby a surface of the substrate becomes coated with the active coating material; and dividing to form individual dosage units.

101. A method of coating a substrate which is a belt, sheet, film, or tape, the method comprising the steps of preparing a pharmaceutical product by applying one or more coating layers to the substrate, the layer or the first layer being applied directly to a surface of the substrate, the layer or at least one of the layers comprising active coating material, the active coating material comprising biologically active material, wherein the active coating material is applied electrostatically as a powder and after the active coating material is applied the active coating material is fused to form an active film layer, and wherein the layer or layers applied are removable from the substrate as a coherent layer or layers and wherein the layer or layers applied are removed from the substrate as a wafer comprising the active film layer and divided into portions.

102. The method according to claim 101, wherein the substrate is pre-coated with one or more coating layers removable from the substrate and the active coating layer is removable therewith.

103. The method according to claim 101, which includes the step of applying a cover coating material onto the active coating layer to form a cover coating layer wherein the active coating layer is substantially completely covered by the cover coating layer, and wherein that cover coating layer is removable from the substrate.

104. The method according to claim 103, wherein the cover coating material is applied electrostatically as a powder and after application is fused to form a cover film coating.

105. The method according to claim 103, wherein the cover coating layer is removable with the active coating layer.

106. The method according to claim 103, wherein the cover coating material includes biologically active material.

107. The method according to claim 103, wherein the method further includes the step of applying a further coating material to a surface of the substrate to form a further coating layer wherein the further coating layer is removable from the substrate.

108. The method according to claim 107, wherein the further coating material includes biologically active material, the further coating layer forming a further active coating layer and the method further includes the step of applying a further cover coating material onto the further active coating layer to form a further cover coating layer wherein the further active coating layer is substantially completely covered by the further cover coating layer and wherein the further cover coating layer is removable from the substrate.

109. The method according to claim 108, wherein the active material of the active coating layer and the further active coating layer are the same.

110. The method according to claim 103, wherein the method includes the step of applying a second active coating layer onto a surface of the substrate, the second active coating layer forming a second active coating region on the surface of the substrate, the second active coating layer being removable from the substrate, and applying a second cover coating layer onto the second active coating layer to form a second cover coating layer wherein the second active coating layer is substantially completely covered by the second cover coating layer, the second cover coating layer being substantially separate from the first cover coating layer, and being removable from the substrate.

111. The method according to claim 101, which comprises applying to the substrate a base coating layer, applying the active coating material to the base coating layer and applying a cover coating layer over the active coating layer, the three layers being removable together by peeling from the substrate in the form of a three-layer wafer.

112. The method according to claim 111, wherein the base coating layer and the cover coating layer are each applied electrostatically as a powder and each fused to form a film.

113. The method according to claim 101, wherein at least 90% by weight of the particles of the active coating material have a particle size in the range of from 1 to 45 microns.

114. The method according to claim 101, wherein 90% by weight of the particles have a size less than 70 microns, 50% by weight have a size less than 40 microns and 10% by weight have a size less than 10 microns.

115. The method according to claim 101, wherein the method comprises supporting the substrate adjacent to source of the active coating material with a surface of the substrate maintained at such a different electric potential from that of the active coating material that the application of the electric potential causes the active coating material to move from the source of the active coating material towards the substrate, a surface of the substrate becoming coated with the active coating material.

116. The method according to claim 101, wherein the substrate is supported from above and the powder moves from the source upwards towards a lower surface of the substrate.

117. The method according to claim 101, wherein the portion into which said layer or layers are divided contains substantially one dose of the active material.

118. The method according to claim 101, wherein the active coating material is applied to a plurality of individual regions on the surface of the substrate.

* * * * *